United States Patent [19]

Protas et al.

[11] Patent Number: 5,718,223
[45] Date of Patent: Feb. 17, 1998

[54] ANESTHESIA DELIVERY SYSTEM

[76] Inventors: Kenneth S. Protas, 3292 Belmont Glen Dr., Marietta, Ga. 30067; Fred L. Weitz, 2980 Baker's Meadow La., Atlanta, Ga. 30339

[21] Appl. No.: 442,276

[22] Filed: May 16, 1995

[51] Int. Cl.$^6$ .................................................. A61B 5/02
[52] U.S. Cl. .............................. 128/204.21; 128/204.18
[58] Field of Search .................... 128/204.21, 204.18; 364/413.01, 413.02, 413.03, 413.04, 413.05

[56] References Cited

U.S. PATENT DOCUMENTS

| | | | |
|---|---|---|---|
| 4,315,309 | 2/1982 | Coli | 364/413.02 |
| 4,853,521 | 8/1989 | Claeys et al. | 235/375 |
| 4,878,175 | 10/1989 | Norden-Paul et al. | 364/413.01 |
| 5,199,439 | 4/1993 | Zimmerman et al. | 364/413.02 |
| 5,265,010 | 11/1993 | Evans-Paganelli et al. | 364/413.02 |
| 5,315,505 | 5/1994 | Pratt et al. | 364/413.01 |
| 5,319,543 | 6/1994 | Wilhelm | 364/413.02 |
| 5,432,698 | 7/1995 | Fujita | 364/413.02 |

OTHER PUBLICATIONS

International Journal of Clinical Monitoring and Computing vol. 7, 1990 Subramanian et al, "Automated Anesthesia Surgery Medical Record System" pp. 259–263.

Anesth Analog. vol. 68, 1989 Strauss et al, "A Computerized Anesthesia Database" pp.340–343.

Minerva Anestesiologich vol. 59 No. 10 Oct. 1993, Gregorini et al, "Registrazione Computerization Deiparametri Fistolayrei Monitorizzati Durante anestesia" pp. 493–498.

Journal of Biomedical Engineering vol. 3, No. 3 Jul. 1981, Harrison et al. "Codifications of Anaesthetic Information for Computer Processing".

International Journal of Clinical Monitoring and Computing vol. 12, 1995 Heinnichs, "Automated Anaesthesia Record System, Observations on Future Trends of Development" pp. 17–20.

*Primary Examiner*—Vincent Millin
*Assistant Examiner*—William J. Deane, Jr.
*Attorney, Agent, or Firm*—Richard L. Strauss, Esq.

[57] ABSTRACT

The present invention discloses a method for efficiently recording and entering multiple anesthetic treatment variables, including all the data conventionally recorded in an anesthetic record, as well as anesthesia outcome data, into an integrated computer data base. The data base is thereafter subjected to trend analysis to identify any statistically significant nexus between treatment variables with sub-optimal outcomes. Accurate cost trend information is also provided. In preferred embodiments of the present invention, the required use of standardized practice protocols are disclosed in a method that optimizes the identification of any such nexus. Thus, the disclosed method provides accurate information useful for the modification and improvement of delivered anesthetic care.

30 Claims, 10 Drawing Sheets

| REVERSAL AGENTS | | | | INVASIVE MONITORS | |
|---|---|---|---|---|---|
| ATROPINE | AT | mg | 0-20 | ARTERIAL LINE | ART |
| EDROPHONIUM | EH | mg | 0-100 | CARDIAC OUTPUT | C.OUT |
| GLYCOPYRROLATE | GL | mg | 0-1.0 | CENTRAL VENOUS | |
| NEOSTIGMINE | NS | mg | 0-10.0 | PRESSURE | CVP |
| PYRIDOSTIGMINE | PY | mg | 0-25.0 | DOPPLER | DOPP |
| | | | | ELECTROENCEPHALOGRAM | EEG |
| AIRWAY | | | | EVOKED POTENTIALS | EVOKED |
| ANODE/ARMORED TUBE | ANO | | | OXIMETRIC SWAN GANZ | |
| BAIN/MAPLESON D | BAIN | | | CATHETER | OXIMET.SG |
| EMDOBRONCHIAL TUBE | EBT | | | SWAN GANZ CATHETER | S-GANZ |
| ENDOTRACHEAL TUBE | ETT | | | | |
| FIBEROPTIC | F.OP | | | SWAN PACING WIRE | P.WIRE |
| LASER FLEX TUBE | L.FL | | | | |
| LMA | LMA | | | INTRAVENOUS LINES | |
| LTA | LTA | | | INTRAVENOUS #1 | IV1 |
| MEROCEL LASER WRAP | MER | | | INTRAVENOUS #2 | IV2 |
| NASAL AIRWAY | NAW | | | INTRAVENOUS #3 | IV3 |
| NASAL CANNULA | NC | | | INTRAVENOUS #4 | IV4 |
| NASAL RAE TUBE | N.RAE | | | | |
| ORAL AIRWAY | OAW | | | REGIONAL ANESTHESIA | |
| ORAL RAE TUBE | O.RAE | | | ANKLE BLOCK | ANK.BL |
| PEEP VALVE | PEEP | | | AXILLARY BLOCK | AX.BL |
| STYLET | ST | | | BLUNT SPINAL NEEDLE | BLUNT |
| | | | | EPIDURAL KIT | EPID |
| MONITORS | | | | IV REGIONAL | IV.REG |
| BLOOD PRESSURE | BP | | | LONG EPIDURAL NEEDLE | LONG.NDL |
| CAPNOGRAPHY | CAPNO | | | OCULAR BLOCK | OCULAR.BL |
| CO2 DETECTOR | CO2.DET | | | PERIPHERAL NERVE | |
| DINAMAP | D.MAP | | | BLOCK | P.NERV.BL |
| DISPOSABLE PULSE | | | | SPINAL BUPIVACAINE | BU |
| OXIMETER | DISP P.OX | | | SPINAL KIT | SPI |
| ELECTROCARDIOGRAM | EKG | | | SPINAL TETRACAINE | TET |
| ESOPHAGEAL STETHOSCOPE | E.ST | | | SPINAL XYLOCAINE | XY |
| PERIPHERAL NERVE | | | | | |
| STIMULATOR | PNS | | | VOLUME EXPANDERS | |
| PRECORDIAL STETHOSCOPE | PCS | | | ALBUMIN 5% | AL5 |
| PULSE OXIMETER | P.OX | | | ALBUMIN 25% | AL25 |
| TEMP. STRIP | T.STRIP | | | HETASTARCH | HST |
| TEMP. ESOPHAGEAL | | | | | |
| STETHOSCOPE | T.E.ST | | | MISCELLANEOUS | |
| | | | | BLOOD WARMER #1 | B.WRM-1 |
| | | | | BLOOD WARMER #2 | B.WRM-2 |
| | | | | EYE LUBRICATION | EYE LUB |
| | | | | FOAM PADS | PADS |
| | | | | GOGGLES | GOG |
| | | | | HEAD REST | H.RST |
| | | | | HUMIDIFIER | HUMID |
| | | | | WARMING BLANKET | W.BKT |

FIG. 2A

NARCOTICS

| | | | |
|---|---|---|---|
| ALFENTANIL | AL | cc | 0-30 |
| BUPRENORPHINE | BU | mg | 0-0.6 |
| BUTORPHENOL | BT | mg | 0-6.0 |
| DEMEROL | DE | mg | 0-200 |
| DILAUDID | DI | mg | 0-10 |
| FENTANYL | FE | cc | 0-200 |
| MORPHINE | MO | mg | 0-30 |
| NALBUPHINE | NL | mg | 0-30 |
| SUFENTANIL | SU | ug | 0-1000 |

VASOACTIVE

| | | | |
|---|---|---|---|
| ATROPINE | AT | mg | 0-2.0 |
| DOPAMINE DRIP | DOP.DRP | | |
| EPHIDRINE | ED | mg | 0-200 |
| EPINEPHRINE | EPI | ug | 0-2000 |
| EPINEHRINE DRIP | EPI.DRP | | |
| ESMOLOL | ES | mg | 0-500 |
| ESMOLOL DRIP | ES.DRP | | |
| GLYCOPYRROLATE | GL | mg | 0-1.0 |
| HYDRALAZINE | HY | mg | 0-50 |
| LABETOLOL | LB | mg | 0-300 |
| LEVOPHED DRIP | LEV.DRP | | |
| METOPROLOL | MT | mg | 0-50 |
| NICARDIPINE DRIP | N.DRP | | |
| NIFEDIPINE | NF | mg | 0-30 |
| NITROGLYCERINE DRIP | NT.DRP | | |
| NIPRIDE DRIP | SN.DRP | | |
| PHENYLEPHRINE | PH | ug | 0-4000 |
| PHENYLEPHRINE DRIP | PH.DRP | | |
| PROPRANOLOL | PP | mg | 0-30 |

LOCAL ANESTHETICS

| | | | |
|---|---|---|---|
| BUPIVACAINE | BU | cc | |
| CHLORPROCAINE | CP | cc | |
| XYLOCAINE | XY | cc | |

FLUIDS

| | |
|---|---|
| D5 | D5 |
| 1/4 NORMAL SALINE | 1/4NS |
| 1/2 NORMAL SALINE | 1/2NS |
| LACTATED RINGERS | LR |
| NORMAL SALINE | NS |

WEST PACES ANESTHESIA ASSOCIATES, P.C.
☐ WPMC ☐ PAVILION ☐ GASM ☐ OTHER

| DATE | SURGEON |
|---|---|
| DIAGNOSIS | |
| PROCEDURE | |
| ANESTHETIST | ANESTHESIOLOGIST |

{ 31

ANES.    START    SURGEON START    SURGEON END    ANES. END
         ☐☐       ☐☐               ☐☐             ☐☐
         ☐☐       ☐☐               ☐☐             ☐☐

GEN. ANES: ☐ MASK/LMA  ☐ EPID. ANES.  ☐ SPINAL ANES.  ☐ BR. PLEXUS  ☐ PERIPH. N.  ☐ MAC
           ☐ INTUBATED

☐ LABOR EPIDURAL    START    STOP
                    ☐☐       ☐☐
                    ☐☐       ☐☐

☐ ASA I   ☐ ASA II   ☐ ASA III   ☐ ASA IV   ☐ ASA V

PAIN SERVICE DATES:

| MODIFIERS: | MONITORS: | MISC: | PAIN: |
|---|---|---|---|
| ☐ EMERGENCY | ☐ CAPNOGRAPHY | ☐ HYPOTENSIVE | ☐ PCA |
| ☐ AGE(<1 OR >70) | ☐ ARTERIAL LINE | ☐ FIBEROPTIC INTUB. | ☐ EPID. PLACEMT/POSTOP PAIN |
| ☐ FIELD AVOIDANCE | ☐ BLOOD GAS | ☐ ONE LUNG ANES. | ☐ EPID. SETUP/POSTOP PAIN |
| ☐ POSITIONING | ☐ CVP | ☐ CHANGE POSITION | ☐ ____ FOR POSTOP PAIN |
| | ☐ SWAN GANZ | ☐ MD ASSIST | ☐ EVAL-COMPLEX |
| | ☐ CARDIAC OUTPUT | ☐ ANES. ASSIST | ☐ EVAL-STD. |

INTRAOP/POSTOP QA INDICATORS:

MAJOR MORBIDITY: (WITHIN 48 HOURS)
- ☐ DEATH
- ☐ CARDIO PULMONARY ARREST
- ☐ MYOCARDIAL INFARCTION
- ☐ CVA
- ☐ SEIZURE
- ☐ ANAPHYLAXIS

AIRWAY:
- ☐ FAILED INTUBATION
- ☐ DIFFICULT INTUBATION (> 2 ATTEMPTS BY MD OR UNPLANNED FIBEROPTIC)
- ☐ TRAUMA (INCLUDING DENTAL)
- ☐ ASPIRATION
- ☐ REINTUBATION

LINE COMPLICATION:
- ☐ PNEUMO OR HEMOTHORAX
- ☐ OTHER

REGIONAL ANESTHETIC:
- ☐ FAILED REGIONAL
- ☐ INADVERTENT DURAL PUNCTURE
- ☐ LOW PRESSURE HEADACHE

NERVE INJURY/DEFICIT:
- ☐ AFTER GEN. ANES.
- ☐ AFTER REGIONAL ANES.

DELAY: (>15 MIN. STARTING)
- ☐ SURGEON
- ☐ ANES/LINE PLACEMENT
- ☐ ANES/REGIONAL ANES.
- ☐ ANES/OTHER ______
- ☐ OR STAFF
- ☐ OTHER
- ☐ OTHER

OTHER:

---

PACU

- ☐ NAUSEA (>1 MED. ATTEMPT)

PROLONGED STAY:
- ☐ NAUSEA
- ☐ SEDATION
- ☐ PAIN
- ☐ REGIONAL
- ☐ OTHER ANES. COMP.
- ☐ NON-ANES. COMP.

UNPLANNED ADMISSION:
- ☐ NAUSEA
- ☐ SEDATION
- ☐ PAIN
- ☐ REGIONAL
- ☐ OTHER ANES. COMP.
- ☐ NON-ANES. COMP.

MISC.
- ☐ CORNEAL ABRASION
- ☐ HYPOTENSION (REQ. PRESSOR)

PACU TIMES:
ADMIT ☐☐  DISCHARGE ☐☐
DISCHARGE: ☐ HOME  ☐ ______ ROOM

ANESTHESIA DELIVERY SYSTEM

TECHNICAL FIELD

The present invention relates to the field of computer enhanced medical care delivery. More specifically, the present invention relates to a method of delivering anesthesia service wherein anesthesia application is continually modified in accordance with information generated from trend analysis of recorded data.

BACKGROUND OF THE INVENTION

The field of anesthesia has undergone profound changes during the latter part of the twentieth century. Among the most significant improvements in this medical discipline have been the introduction of new pharmacological agents providing greater control of the degree and duration of anesthesia while providing improved safety.

In operative anesthesia, a defined group of pharmacological agents are utilized to tranquilize the patient, block pain perception, induce sleep, relax muscles and maintain a deep state of unconsciousness. Other agents are utilized to control common anesthesia side effects such as, nausea. Other medications may be utilized to control blood pressure and coagulation. The terms practice "protocol", "algorithm" and "regimens" refer to anesthetic routines comprising lists of specific pre-operative medications, induction agents, narcotics, relaxants and maintenance agents. These terms also refer to the dosage and delivery techniques utilized with these agents.

Anesthetic protocols are designed to address particular difficulties and requirements of a given anesthetic situation. Agents utilized in anesthetic protocols often have profound effects upon the circulatory, respiratory and nervous systems. Unfortunately, these effects occasionally lead to "sub-optimal" anesthesia events ranging from simple nausea and prolonged hospital stay to death. Also, the metabolism and clearance of different agents follow different organ and system pathways. Therefore the general systemic health of each patient, as well as specific organ function status are important factors in selecting appropriate agents. The particular nature and duration of the surgical procedure to be accomplished must also be taken into consideration in selection of agents.

Private and public (non-academic) practices also vary their anesthetic protocols. Typically, at this level of practice, well known and approved agents are substituted for others within a known protocol in order to improve the effectiveness and safety of care delivery provided for a given class of patient or procedure. Delivery technique and dosages are also modified, within safe and proscribed limits, in an attempt to achieve these same goals. Non-academic protocol development is most often the result of an identified difficulty encountered in practice.

The fact that anesthesiologists practicing within the same group will typically, while providing anesthetic care in substantially similar situations (same class of patient type, history and procedure), utilize widely differing protocols, further complicates the task of identifying positive, statistically significant, agent/outcome relationships. Non-standardized practice greatly reduces the chance of identifying a sub-optimal result related to a given protocol. The anesthetic factors of patient type, history and procedure will always remain variables. Since practitioners within the group are not utilizing standardized algorithms, few constants for postulating cause and effect remain. Thus causative trends between algorithms and sub-optimal results are not easily identified. Therefore modification and improvements upon protocols to improve safety and effectiveness are difficult and often speculative.

Unfortunately, current anesthetic practice does not incorporate a systematic and fully effective means to identify sub-optimal anesthetic results related, by statistically significant percentages, to practice algorithms or the agents and techniques therein. The term "statistically significant" as utilized in this application, refers to numerical relationships or functions between factors, subject to analysis, that are beyond what would be expected by normal experience or mere random chance. Current methodology also does not disclose a means for efficiently recording and formatting, for analysis purposes, all of the variable factors required to identify such positive, statistically significant relations or trends. Existing record techniques, both manual and computer assisted, simply do not provide a simple, user friendly method of such recording and entry. What is needed is an efficient method of recording and entering intra-operative, as well as post-operative, anesthesia data into a computerized data base wherein accurate trend analysis could be performed. Thereafter, intelligent modification of anesthesia protocols could be effected to improve the quality of care and reduce the degree and frequency of sub-optimal anesthesia events.

Automated anesthesia records systems are known. For example, U.S. Pat. No. 4,853,521, (the '521 patent) discloses an automated record generating system configured for use in anesthetic practice. This system utilizes bar codes, affixed to agent syringes, containers and vaporizer controls in order to automate production of an anesthetic record. However, the process is cumbersome as it requires placement of bar codes on all agent syringes as well as placement of bar code readers within the surgical suite. The anesthetic recording process disclosed by the '521 patent differs substantially from existing conventional formats and thus requires substantial provider training.

The '521 patent does not disclose user friendly, automated, post surgical outcome data recording. Furthermore, the system does not suggest or disclose the creation of a database, comprised of both outcome and cost data. This is not surprising as the '521 patent does not suggest subjecting an outcome/cost database to trend analysis for the purpose of refining practice protocols.

During the last decade, the costs of surgery have literally exploded. At the same time, the available resources for paying the price of such care have dwindled. It has therefore become imperative to increase the efficiency of delivered surgical care. A large percentage of surgical cost is due to necessary anesthesia services. The anesthetic agents and anesthesia related consumable materials utilized are likewise responsible for a large proportion of these costs.

The cost of individual agents utilized within a protocol may vary tremendously. Yet, at the same time, a substantially less expensive agent, with equal safety and effectiveness, may be available. However, identification of the more economical choice from two "substantially equivalent" agents is not always readily apparent. Although cost per unit dose may be easily discerned, the factors of actual effective application dosage, alteration and effect upon other agents, and duration of effect make such choices less than obvious.

An anesthesia department might choose to utilize less expensive "equivalents agents" in various protocols. However, these modifications, are not presently based upon analysis of a comprehensive anesthetic experience data base.

Thus, agent substitution is, at best, based upon an educated guess of cost. At the present time, no method or system has been disclosed, which provides for the recording and automated entry of anesthetic cost data. Furthermore, no method has been disclosed which provides for cost trend analysis of anesthetic protocols or the agents and materials utilized therein.

SUMMARY OF THE INVENTION

It is an object of the present invention to provide a method for accurately recording, entering and analyzing all of the data ordinarily recorded in an operative and post-operative anesthetic record wherein relations between anesthetic variables and sub-optimal outcomes are identified and thereafter utilized to modify delivered anesthetic care. Therefore, it is an object of the present invention to provide a method for constantly refining and improving the delivery of anesthesia services.

More specifically, it is an object of the present invention to provide a method for accurately recording and electronically entering, into an integrated computer database, all of the data ordinarily recorded in an operative anesthetic record. It is a further object of the present invention to provide for computerized trend analysis of said database for the purpose of creating trend reports to identify any nexus between protocols, and the agents, materials and techniques therein, with sub-optimal outcome events. It is a further object of the present invention to enter cost data into said database so as to enable protocol/cost data trend analysis. Thus, it is the object of the present invention to provide a method and system that provides the information necessary to accurately and continuously refine anesthetic protocols in order to yield safer, more effective and efficient anesthesia service.

Now in accordance with the present invention, a new method of providing anesthetic care is disclosed wherein a computerized recording and monitoring system, dedicated to tracking substantially all major anesthetic variables, is provided.

In one embodiment of the present invention, a method of delivering anesthetic care is disclosed wherein a record of patient A.S.A. type (American Society of Anesthesiologists), continuous medical condition, surgical procedure, as well as the identity, dosage, amount and means of administration of all administered agents is created. Outcome data for each anesthetic procedure is also recorded. The recorded data is entered into an integrated computerized data base for each and every anesthetic case. The data within the data base is then subjected to computerized trend analysis in order to identify any nexus between protocols, (including the agents, materials and techniques therein) and suboptimal results;

When trend analysis indicates a positive, statistically significant relation between a protocol factor (specific agent, dosage/perfusion or administration technique) the protocol is altered, in accordance with sound principles of anesthesia, in order to eliminate sub-optimal results. Such modifications may, for example, involve substitutions of agents, changes in dosages/perfusion rates and/or alteration of administration technique.

In a first alternate embodiment of the present invention, a method of providing anesthetic care is disclosed further comprising selecting standardized practice protocols. In practicing the first alternate method of the present invention, only an appropriate protocol, restricted to one selected from the standardized protocols, is chosen for application in a particular case. Selection and restriction of practice to the use of standardized protocols provides a uniform practice method. Thus reliable analysis of protocol performance can be rapidly and easily attained by virtue of the frequency of uniform application thereof.

In a second alternate embodiment of the present invention, a method of delivering anesthetic care is disclosed wherein accurate cost tracking and control of agents and materials utilized is provided. In practicing the second alternate method, a record of patient medical type, continuously monitored condition, and surgical procedure is created. The identity, dosage, amount and means of administration of all administered agents are also recorded. A record of all other anesthesia materials consumed is also made. For example, cost data for materials such as catheters, I.V. bags and other consumable materials is recorded. The recorded data is entered into an integrated computerized data base. Continuously updated agent cost data is also entered therein. The data base is subjected to a computerized cost analysis wherein a true cost analysis of protocols and agents is provided. The cost analysis also provides data for comparison of "equivalent" agents as well as providing accurate billing information. The protocols are thereafter altered, in accordance with the trend analysis, to include less costly agents that are substantially equal in effectiveness as compared to the more costly agents they replace.

In a third alternate embodiment of the present invention, a method of delivering anesthetic care is disclosed wherein outcome trend information, as well as accurate cost tracking and control is provided. In practicing the third alternate method, information related to the medical type, continuous medical condition and surgical procedure performed is recorded. The identity, dosage, amount and means of administration of all administered agents, consumable anesthesia related materials, as well as outcome data are also collected for each anesthetic case. All of the information recorded is entered into an integrated computer data base. Continually updated agent and consumable cost data is also entered therein. Thereafter, the data base is subjected to both the outcome trend analysis as well as cost analysis described above. The protocols, agents and procedures are then altered in order to reduce sub-optimal outcomes and decrease the cost of delivered care.

Each of the embodiments of the present invention may advantageously comprise the additional step of selecting a standardized protocol list and restricting practice to application of the standardized protocols only. Such restriction increases the likelihood of identifying protocol related sub-optimal outcome difficulties through increased frequency of uniform protocol "testing". Standardized protocols increase the accuracy of cost analysis by increasing repeated data base experience. In all cases, sound principles of anesthesia are utilized to modify protocols.

Each of the embodiments of the present invention advantageously contemplate the additional step of recording and entering anesthesia provider data. Such information is helpful in identifying either cost or outcome results that relate to practitioner performance.

In practicing the methods of the present invention, it is highly advantageous to record data contemporaneously with each particular event. Such immediate recording minimizes errors due to time-based memory lapse. In order to facilitate contemporaneous data entry, the methods of the present invention most advantageously include the additional step of entering the data to be recorded upon scanable records that are specifically formatted for highly efficient data entry of all factors to be recorded. For example, a scanable record is most effectively formatted so as to be substantially similar to conventional anesthetic records. Therefore, little or no additional time is required to train providers how to utilize the records while simultaneously providing a record compatible with automated data entry.

The scanable record advantageously includes comprehensive outcome information tracking of both operative as well as post-operative events. The record also includes patient type, continuous medical status, procedure, and all protocol information. Also included is all of the data ordinarily entered within an anesthetic record such as, for example, fluid output and input, blood pressure, pulse, and blood gas data.

In certain embodiments of the present invention, readers are advantageously selected to be of the telefacsimile type. The data stream provided by the reader can thus be transmitted to, for example, a server fax/modem means within, or adjacent to, a central computer processing unit. The central processor is advantageously configured to utilize, for example, an intelligent reader software program.

The intelligent reader program is especially configured to scan only specified areas of the scanable record wherein the above-described variable data is recorded. The program attributes a user selected confidence level to the scanned data and "flags" operator attention to any situation in which the data scanned from the recorded is of questionable accuracy. In low confidence situations, an image of the scanable record is displayed on a monitor or printed at the central processing unit for human confirmation of data entry. The intelligent reader program is also selected to be a type capable of discerning hand written data entries as well as simple blocking/shading entries. Thus the reader program enhances the method of the present invention by allowing the scanable record to incorporate both high speed manual shading data recording as well as conventional alphanumeric recording.

After the data is scanned by the intelligent reader and, if required, is confirmed or modified by a data entry person, the data is transmitted to a central data base storage unit. The storage unit provides both long term data storage as well as an addressable memory source for analysis purposes.

In other embodiments of the present invention, it is advantageous to utilize computer terminals and monitors located, for example, within the operating room and recovery areas for recording anesthetic data. In one embodiment, the computer terminals incorporate CRT or LCD monitors providing anesthetic record displays similar in format to the scanable record. A light pen, mouse or other reader/pointing device is advantageously utilized to enter data utilizing the monitor display. The data entered at the terminal is thereafter transmitted to a central computer processing unit and central storage device.

In practicing the method of the present invention, outcome and cost trend analysis is advantageously accomplished within a computer processing unit linked to a central data storage device. A central server computer linked to a plurality of work station computers is advantageously utilized for trend analysis of the data base. It is also contemplated that multiple facilities can be employed to transmit data via readers and terminals to one central processing location where all data and processing functions occur. Such an arrangement is highly advantageous in that the increased data base provided thereby will increase the probability of identifying outcome and cost difficulties for correction thereof.

BRIEF DESCRIPTION OF THE DRAWINGS

FIG. 2a illustrates a key table located on a reverse side of the scanable anesthetic record illustrated in FIGS. 1a, 1b, 1c and 1d.

FIG. 2b is a continuation of the key table illustrated by FIG. 2a.

DETAILED DESCRIPTION OF THE PREFERRED EMBODIMENT

The present invention relates to an improved method of delivering anesthetic care wherein all anesthesia practice parameters are recorded, and thereafter stored in an integrated computer data base. The data is processed by means of an electronic computer to provide trend indicators. These indicators are thereafter utilized to modify and improve the safety, efficiency and quality of delivered anesthetic care.

In the preferred method of the present invention, anesthetic data is recorded utilizing a scanable anesthetic record. The scanable record advantageously utilizes a format similar to conventional records, but is especially configured to incorporate format designed to simplify and accelerate data recording and entry. For example, the scanable record advantageously utilizes bubble shading, uniform agent codes and uniform dosage units to improve the ease and reduce the effort in producing an accurate anesthesia record. At the same time, such formatting and uniformity enhances the efficiency with which the record may be scanned.

FIG. 1 illustrates an example of a scanable anesthetic record advantageously utilized in practicing the preferred method. The record is comprised of vertically aligned columns and horizontally aligned rows. The first column, 1 is located at the left-most border of the record. At the uppermost portion of column 1, an agent section 3 contains a listing of various general anesthetic, inductive, sedative, muscle relaxant and vasoactive agents. Local anesthetics are also listed. Each agent is represented by an appropriate abbreviation code. For example "DEF" 5, refers to the anesthetic agent Desflurane. Each coded agent includes an associated "bubble", e.g., 7. By shading the bubble adjacent the coded agent, scanable data is provided indicating that the agent has been utilized during an anesthetic procedure. For example, in FIG. 1, shaded bubble 7 indicates desflurane has been utilized. A plurality of time/dose recording columns 9 are located to the right of the agent column.

The dose columns are utilized for recording administered dosages of the agents at precise time intervals during the course of a case. Each of the dose columns is, in turn, divided into three 5 minute time units 11. For each of the 5 minute time units, two blocks are provided for entry of dosage data. For example, at the third row 13 from the top of the record, at the second column, six blocks appear 15. The two left most of these time blocks are utilized to indicate the administration of desflurane at a flow rate of 1.0 liters during the first 5 minute time period of anesthesia.

Changes of the flow rate of anesthetic gases are entered along the time column at any point in time that the flow rate is changed. If a change in the type of inhalation agent utilized occurs during a case, a change bubble 16 is shaded to indicate such change. The concentration of the new inhalation agent is noted along the time columns with agent identifier letters entered just to the left of the noted concentration. Specific notes as to the time and nature of the change may also be additionally entered in the case notes section 27. For intravenous agents, the dose administered is recorded at the time blocks corresponding to the time of administration.

Figure 2B:
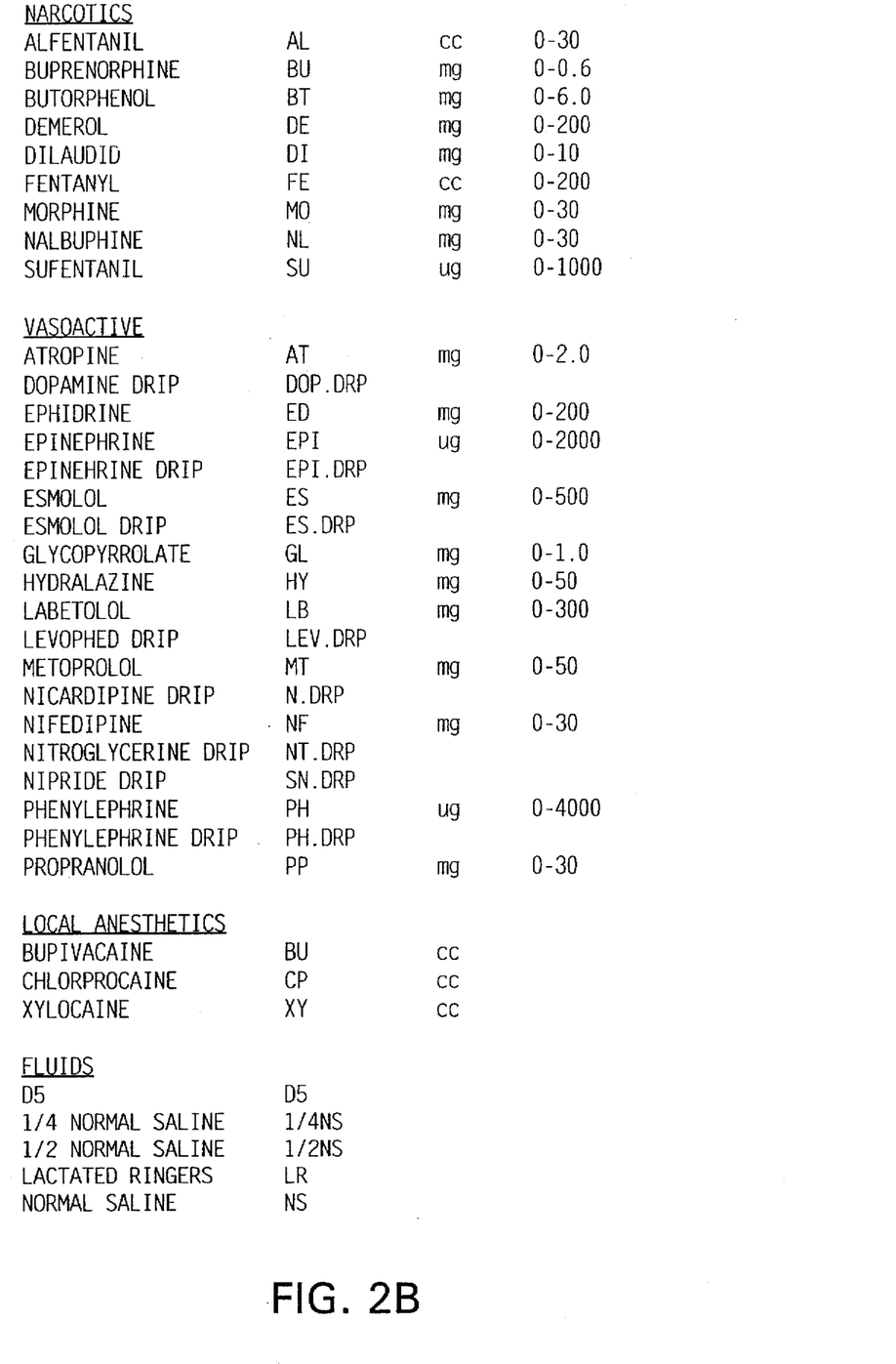

Units of dosage such as liter, milligrams etc. are utilized as appropriate for the agent utilized and indicated in the agent column. However, the units are standardized according to a key table located on a reverse side surface of the anesthesia record. FIGS. 2a and 2b illustrates an example of such a key table. The key includes appropriate identifier symbols for agents as well as the standardized units utilized in record entries. Dosage is entered within 2 blocks of the time column utilizing numeric values. Identity of an agent administered simply requires shading the appropriate agent bubble. To the right of the time/dose columns a total column 17 is utilized to record the total dose of administered agents by the end of a case.

Below the agents section of the first column, a second section, 19, lists various vital parameters including EBL (estimated blood loss), urine, temperature, electrocardiogram, and oxygen saturation. Entries, indicative of a running total, are made in the appropriate time column for estimated blood loss and urine output. Temperature, ECG and oxygen saturation readings are recorded at 15 minute intervals.

A third section 21 of the first column, is provided for the recording of blood pressure values. Entries, along the time line columns, are made continuously during an anesthetic procedure to track the patient's blood pressure. Typically, as in conventional anesthetic records, markings are made at the numerical level of the third section corresponding to the systolic and diastolic pressures of the patient every five minutes. A dot is utilized to indicate patient heart rate.

A fourth section 23 at the left-most column 1, provides for the recording of ET $co_2$ (end tidal $co_2$ tension), TID (tidal volume), RSP (respiratory rate) and $FIO_2$ (fraction of inspired oxygen). As with the first three section parameters discussed above, numeric entries recording these vital signs are made upon the time columns, from left to right, temporally, as the case proceeds.

At the upper right hand section of the record, an identifier section 25 is provided for the recording of messages, page number of record/total number of pages, patient identity, start time of anesthesia, start time of operation, end of operation and end of anesthesia. This section also includes provision for entry of patient diagnosis and planned operative procedure. Bubble entry is provided for indication that anesthesia machines and patient position has been checked. Provision for the recording of the identity of surgeon, anesthetist and anesthesiologist is also made. Also noted are patient height, weight, ASA type, NPO intake notation and pre-medication. Entries are accomplished as direct alphanumeric or bubble shading.

Below the identifier section of the record 25, a notes section 27, is provided for the recording of case notes. Such recording can be accomplished utilizing standard handwritten entries.

A materials and monitors section 29, is provided in the lower right hand corner of the record. This section is utilized for tracking anesthetic materials, such as, for example, catheters, I.V. lines and fluids. Routine and special monitors are also tracked utilizing materials and monitors section. Provision is also made for pressor, reversal and miscellaneous agents. Bubble shading is utilized for quick and accurate notation of materials utilized. However, boxes are also provided 30, for numeric entry of dosage amounts of the agents therein recorded.

Figure 3A:
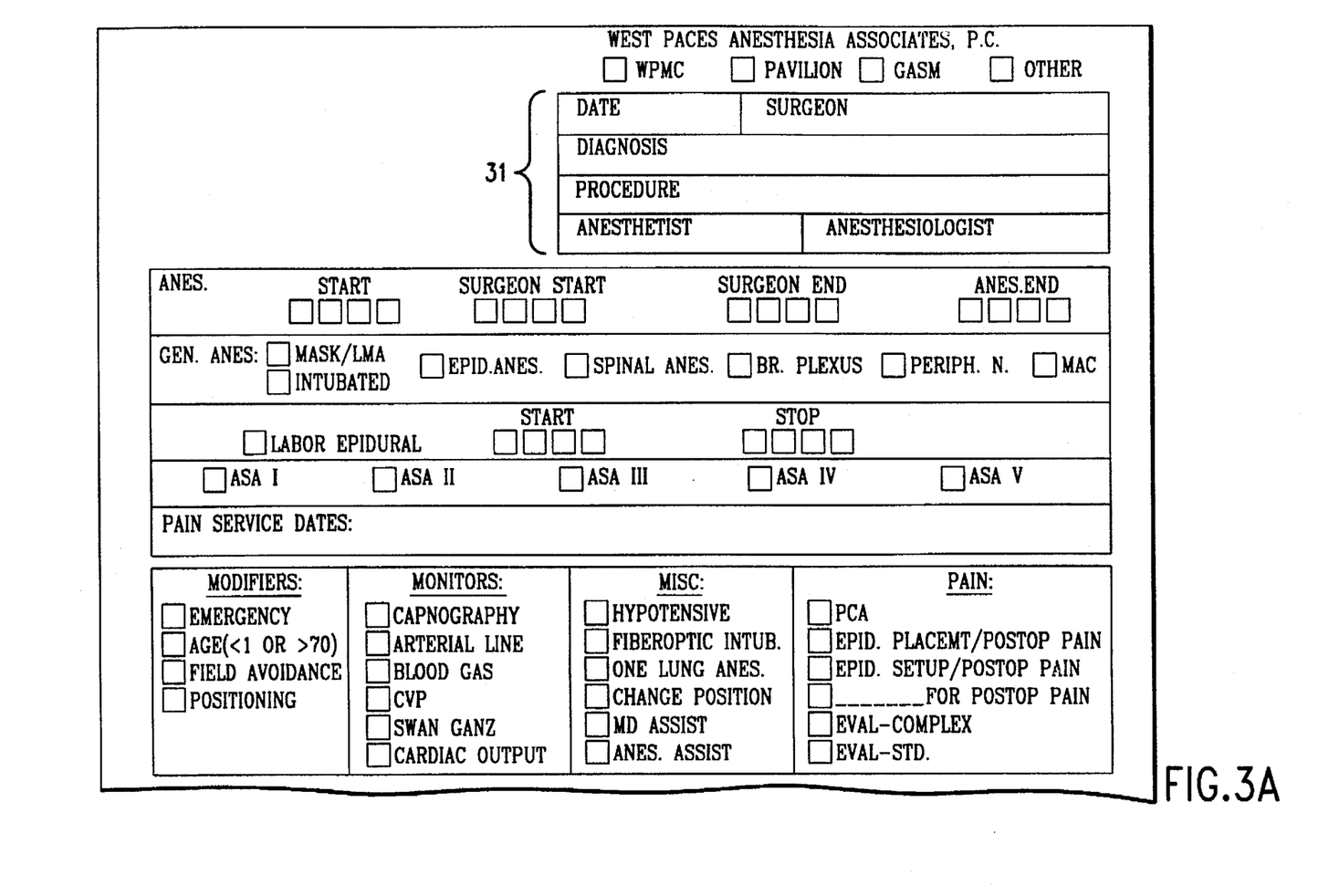
FIG. 3a illustrates an upper portion of an example of a scanable outcome record utilized in practicing the method of the present invention illustrated in its entirety in FIGS. 3a and 3b.
Figure 3B:
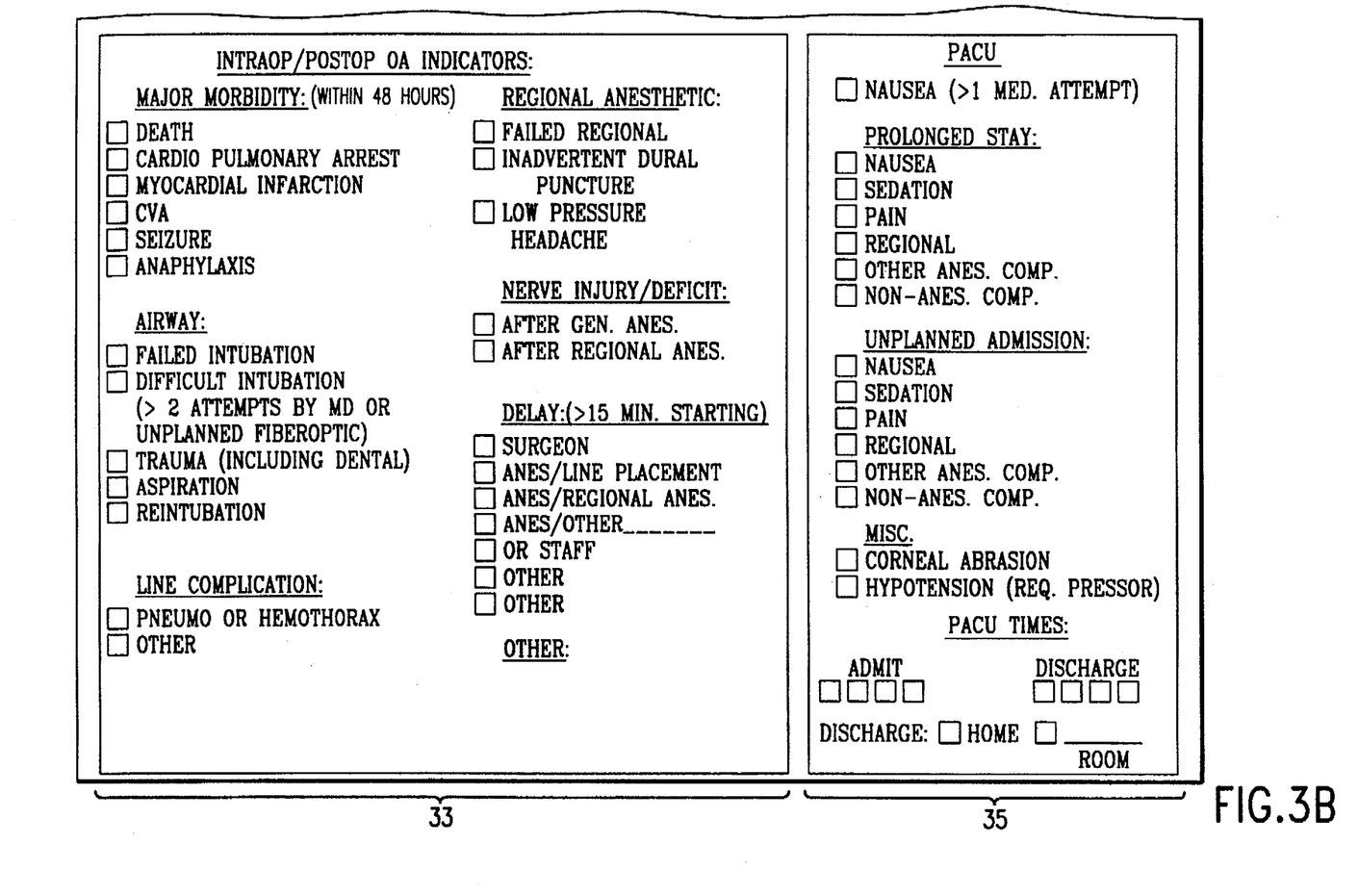
FIG. 3b illustrates a lower portion of an example of a scanable outcome record utilized in practicing the method of the present invention.

FIG. 3 illustrates a scanable outcome record specifically configured and formatted for use in the preferred method of the present invention. The scanable outcome record provides for similar bubble shading/alpha-numeric entry as the scanable anesthetic record described above. The outcome record also includes a section 31 for entry of patient, practitioner and procedure identifiers as included in the anesthetic record.

The scanable outcome record includes a major "INTRAOP/POSTOP QA INDICATORS" SECTION 33 at the lower left hand corner of the sheet. This section utilizes both bubble and alpha-numeric entry for tracking of anesthetic complications during both intraoperative and postoperative time periods. A "PACU", post anesthetic care unit, section 35 is included to track required treatment and sub-optimal effects associated with anesthetic care.

In the preferred method of the present invention, entries within both scanable anesthetic and outcome records are made contemporaneous with recorded events whenever possible. Since the format of the anesthetic record is similar to a conventional record and the outcome record utilizes simple bubble/alphanumeric entry, little practitioner time is required to learn and thereafter utilize a highly detailed record.

Figure 4:
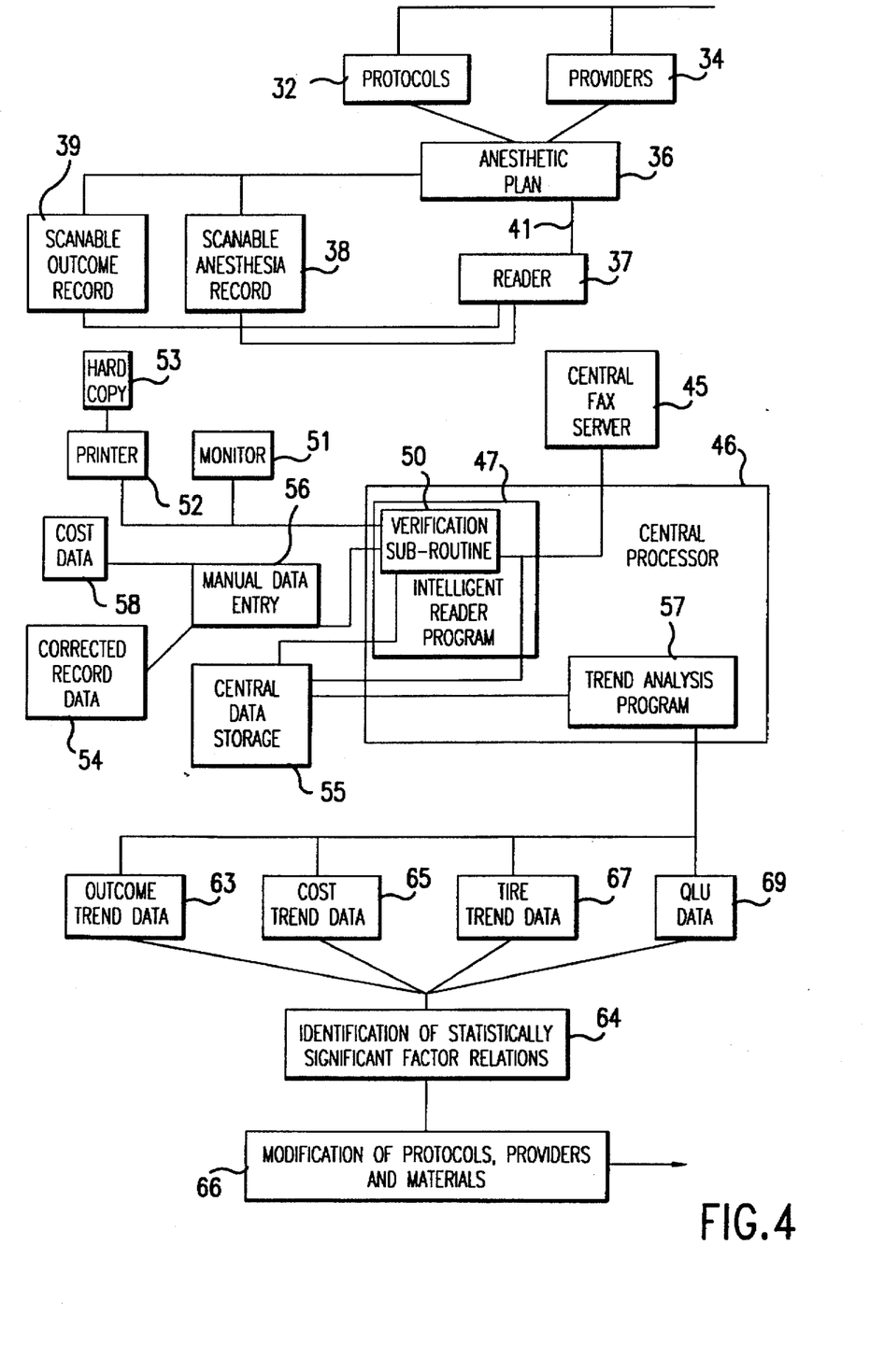
FIG. 4 is a flow chart illustrating the preferred method of the present invention.

FIG. 4 is a flow chart illustrating the preferred method. After completing a preoperative evaluation of a subject patient (and review of the proposed surgical procedure), an anesthesiologist 34 selects an appropriate anesthetic protocol 32. In the preferred method, the protocol is selected from, and restricted to, a standardized set of practice regimens. Thereafter, in view of both the preoperative evaluation and selected protocol, an anesthesia plan 36 is formulated.

The subject patient is anesthetized and maintained in accordance with the anesthetic plan 36. Completion of the scanable anesthetic record 38 is substantially simultaneous with recorded operative events. Following surgery, the patient is brought to a recovery room where he is monitored. Completion of the scanable outcome data record 39 is also accomplished substantially simultaneously with the recovery events recorded. After completion of the scanable anesthetic and outcome records, the records are placed into a reader device 37. In the preferred method, a telefacsimile type reader, located in the operating room, recovery room, or both, is utilized to scan the records. A telefacsimile device, especially useful in practicing the method of the present invention is the Ricoh Model 5600™. The scanable record will typically be printed upon paper of a 15 inch width, a dimension greater than many telefacsimile devices are capable of processing. The large paper format is required in order to place all recorded data on one page in a legible font. The Ricoh Model 5600™ is capable of scanning such large format documents.

A data stream 41 provided by the telefacsimile is transmitted via, for example, telephone wire to a central reader. In the preferred method, the data stream provided by the reader is transmitted to a central fax server device 45. The fax server is essentially a microcomputer system that contains both hardware and software to facilitate the reception of fax images received from multiple telephone lines simultaneously. A fax server, such as American International's "Host Fax"™ is especially well suited for practicing the method of the present invention.

The images received by the fax server are sent to another microcomputer 46 that acts as a central data processing unit. Alternatively, the images may be sent to a file server which in turn provide access to the images for processing by a plurality of work station personal computers. The processor selected as the file server or as a work station PC™ should utilize a processor with a speed equal to or greater than Intel's 486-66™ and operate with a random access memory of at least 16 megabytes.

The images provided by the server fax/modem are "read" by means of an intelligent reader program 47 within the central computer's processing unit. The preferred method requires that the intelligent reader program selected provide: form layout; discrete interpretation of defined data fields within the form; and a verifier routine. The reader program selected for use in practicing the preferred method must also include an export module for writing of the data into the database.

An example of an intelligent reader especially useful in practicing the preferred method is Cardiff Software's Teleform™ product. Teleform™ utilizes BasicScript™ programming language which advantageously allows customizing of the commercial reader program for the specific interpretation and export of the data entered into the scanable record.

Figure 1A:
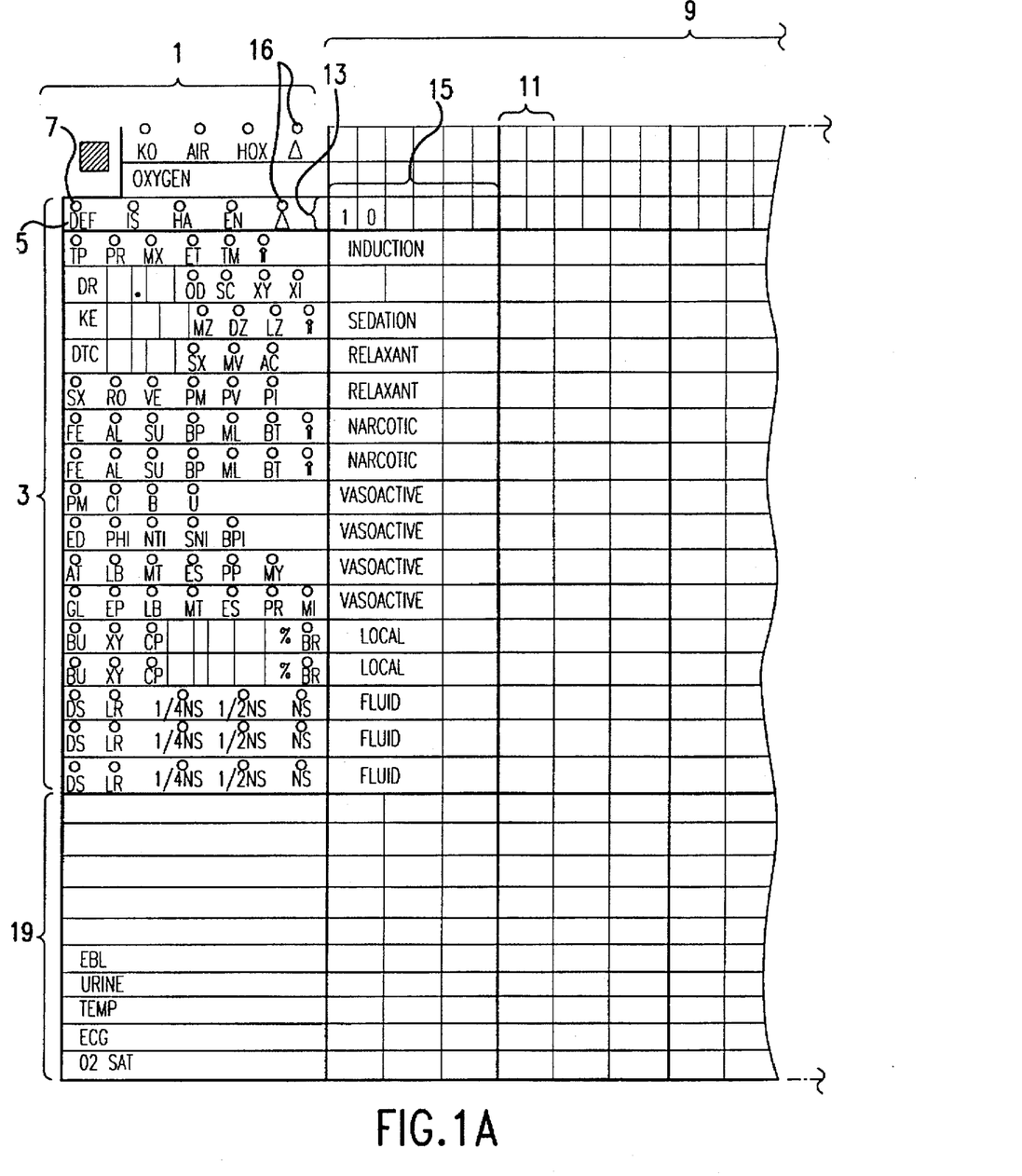
FIG. 1a illustrates an upper left portion of an example of a scanable anesthetic record especially formatted and configured for use in practicing the method of the present invention illustrated in its entirety in FIGS. 1a, 1b, 1c, and 1d.
Figure 1B:
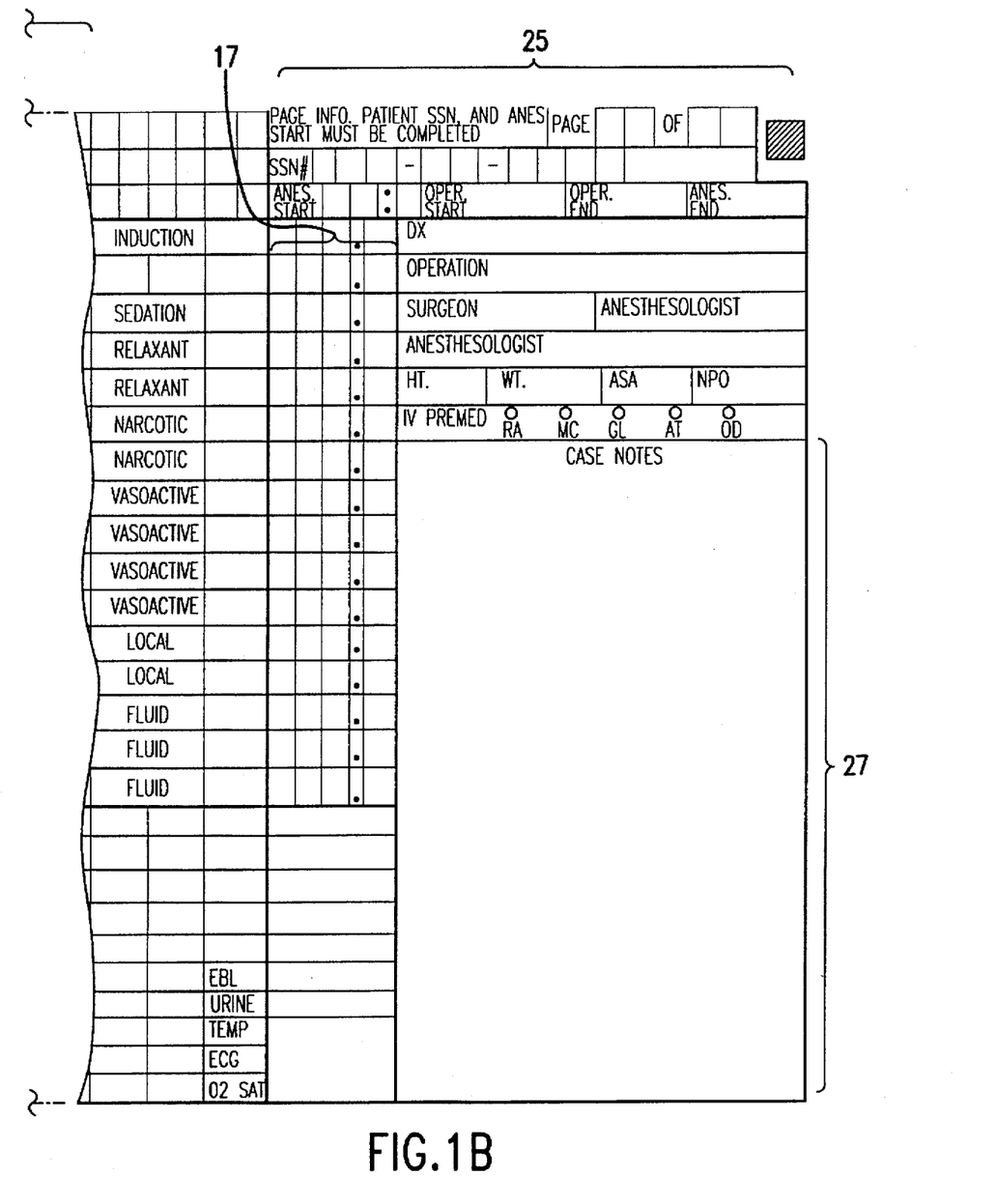
FIG. 1b illustrates an upper right portion of an example of a scanable anesthetic record especially formatted and configured for use in practicing the method of the present invention illustrated in its entirety in FIGS. 1a, 1b, 1c, and 1d.
Figure 1C:
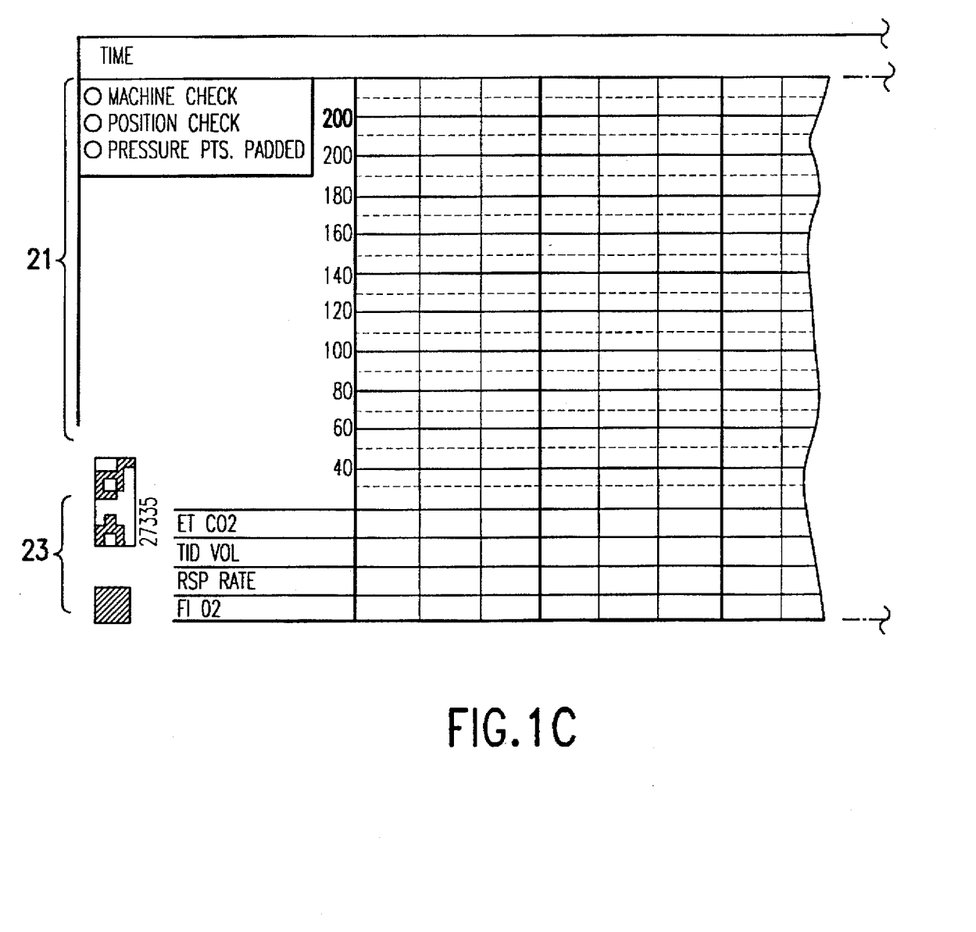
FIG. 1c illustrates a lower left portion of an example of a scanable anesthetic record especially formatted and configured for use in practicing the method of the present invention illustrated in its entirety in FIGS. 1a, 1b, 1c, and 1d.
Figure 1D:
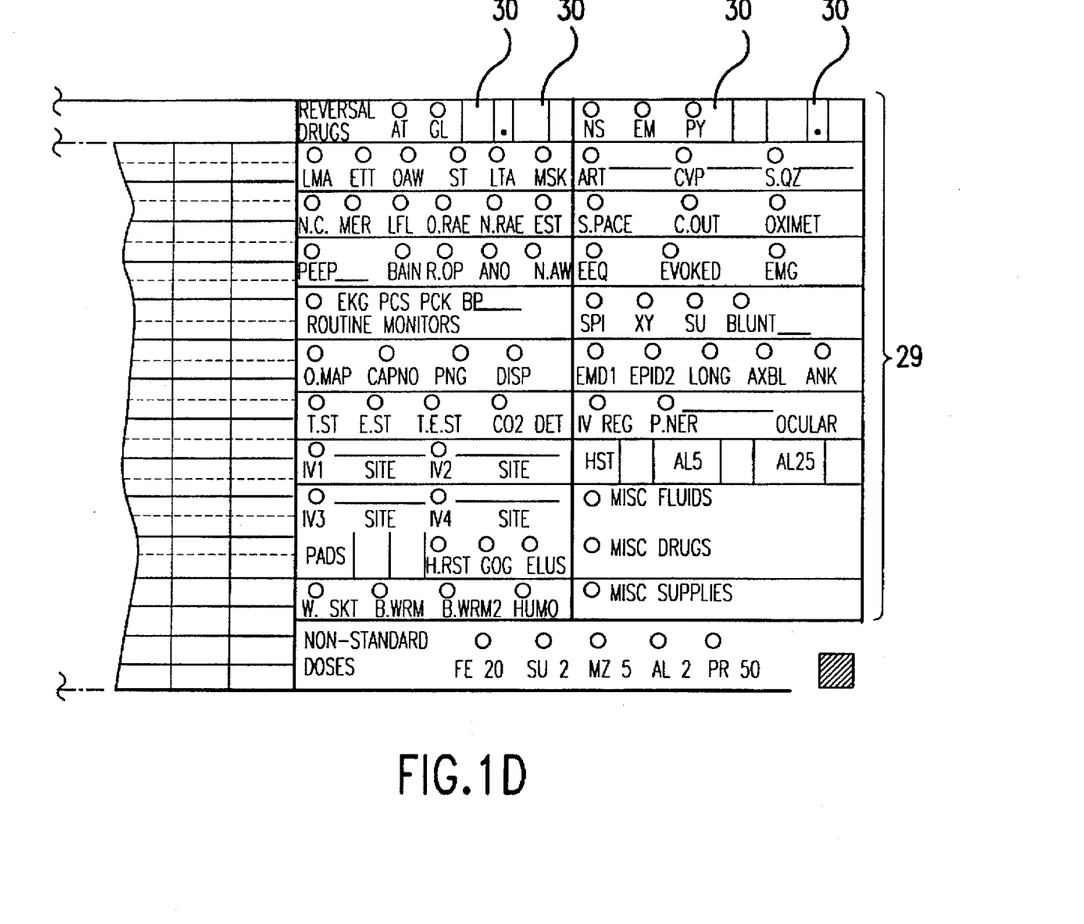
FIG. 1d illustrates a lower right portion of an example of a scanable anesthetic record especially formatted and configured for use in practicing the method of the present invention illustrated in its entirety in FIGS. 1a, 1b, 1c, and 1d.

The intelligent reader program scans only discrete areas of the scanable anesthetic and outcome record in accordance with data entry locations thereon. Non-data entry areas of the records are ignored by the reader program. The intelligent reader program also provides the ability to interpret both shaded bubble entries as well as alphanumeric data. In the preferred embodiment, the reader program includes a verification sub-routine 50 that is configured to detect any ambiguities or "low confidence" situations in reading a faxed record and thereafter activate an alert requiring human verification of read data. If a "change" bubble is shaded on a record, as illustrated in FIG. 1 at 16, indicative of an intra-operative change of anesthetic gas, the included verification routine is also enabled. Thus, data personnel manually verify the correct entry of the specific agent utilized in the change.

A low confidence situation arises when the reader program achieves less than an adjusted threshold of certainty in interpreting recorded entries, or, as discussed above, a change bubble is shaded. In such a case, a verification sub-routine provides a monitor display 51 of a subject virtual anesthesia record as well as, on a split screen thereof, the reader program's interpretation of an uncertain entry or entries. The entry in question is highlighted upon the virtual image for rapid comparison with the interpreted data. A data entry person is then utilized to correct 54, if necessary, the reader programs interpretation of the entry. If, on the other hand, the entry can not be clearly identified, the anesthesia provider who created the record is contacted to obtain accurate information. Optionally, the system allows for printing of a "hard copy" 53 via a local printer 52.

The verification program is also enabled when a scanned record does not include all required entries. For example, failure of a provider to enter totals for all agents utilized, or a failure to note when a particular agent is discontinued will trigger an alarm alerting data entry personnel that the record is incomplete and must be returned to the responsible provider for additional entries.

Thus, read errors/ambiguities are identified and corrected before the data, deciphered by the reader program, is entered 56 into the central database 55 stored in a central data storage device. Data received by the reader not prompting verification passes directly into the database. In practicing the preferred method, it is highly advantageous to utilize, as a central storage device, a hard disc drive with a memory capacity of at least one gigabyte.

In the preferred method, the central data base is provided with data from the scanable records as well as continuously updated cost data 58 for all materials, data, and services.

A software program 57 is especially configured to process and analyze the information collected in the database. Analysis of the data is accomplished at two levels. Both levels provide reports based upon the counting of recorded practice parameters. Simple reports related to the number of events experienced in any recorded category may be provided by subjecting the database to the built-in query tools found in several commercial database access tools. For example, the query tools found in a program such as the Microsoft's Access™ database software package is useful for generating simple reports.

Complex trend analysis reports, utilized for identifying statistically significant relations between recorded variables, may be accomplished utilizing powerful database reporting tools allowing user customized scripts. For example, Crystal Reports™, a powerful database reporting tool, marketed by Seagate Software Company™, may be advantageously applied for such complex trend analysis. The customized scripts of such a program essentially loop through the database and count up or average the various outcome and cost data to be subjected to trend analysis. The program then facilitates the output of these results into a desired printed format. Customized scripts of such database reporting tools are easily keyed to any desired parameter such as, for example, type of procedure, type of drug, etc. The customized scripts are configured to generate reports identifying any statistically significant relation between factors analyzed in accordance with standard known probability formula.

Further analysis of the data provided to the central data base, in terms of the functional relation, or ratios, between analyzed factors, allows refinement of accurate probability projections and models. In practice, the collected data, and analyzed ratios calculated therefrom, are utilized to calculate a statistically significant threshold frequency of occurrence.

Factors which are associated with each other below the threshold value are attributed to random chance. However, factors which are associated at a frequency beyond the threshold are identified as demonstrating a significant functional relation and are reported as such.

Billing information is provided for each case based upon data from the scanned records as well as the cost data manually entered into the data base 56. Such billing records are generated for both central hospital as well as anesthesia department use. The data base is also subjected to five further trend/analytical operations.

An outcome trend analysis 63 is directed at analyzing the relationship between suboptimal anesthesia related results and:

a. anesthesiologist
b. protocol utilized
c. surgeon
d. ASA type
E. Modifiers

The term "modifiers" refers to special anesthetic circumstances which may effect care. For example, emergency procedures, care of infants less than 1 year in age or the extremely elderly, and unusual patient positioning requirements are all categorized as modifier situations. The outcome analysis provides crucial data which indicates statistically significant associations between an anesthetic regimen, provider or surgeon that requires attention. By comparing outcomes with repeatedly flagged suboptimal trend results 64, the offending agent, and or technique is revealed. Thereafter, modification 66 of the selected protocol is utilized to reduce or eliminate the experienced difficulty. Providers who appear in this analysis as associated, by a statistically significant percentage, with a suboptimal trend are reviewed so as to eliminate the possibility that provider technique is the causative factor. Likewise, trend data indicating suboptimal results with particular ASA type patients and situation modifiers is utilized to vary protocol and improve care.

A general cost analysis 65 is directed at comparing the total cost of completed cases by general category. For example, a cost of care comparison is provided to compare the cost of care for:

a. each surgical sub-specialty;
b. procedure type;
c. anesthesia provider;
d. surgeon;
e. practice group and location;
f. ASA classification of patient; and
g. general type of anesthetic.

The term general type of anesthetic refers to categories such as, for example, general anesthesia, epidural, spinal, peripheral nerve block and MAC techniques.

An agents and materials cost trend analysis 67 is directed at comparing the cost of completing cases attributable to agents and supplies utilized:

a. among care providers;
b. within the ASA categories of patients or modifiers;
c. by surgical procedure;
d. by surgeon;
e. by protocol selected When a cost trend analysis indicates a positive, statistically significant relation between a specific protocol and increased anesthetic cost, the protocol is carefully scrutinized. If after such review, an offending agent or technique utilized in the protocol is determined to be effecting the increased cost, an alternative agent or technique is selected, in accordance with sound principles of anesthesia, to eliminate the excessive cost. Care providers demonstrating a positive correlation with increased care cost are similarly scrutinized. Thereafter, if appropriate, changes in technique and/or practice are instituted.

A time trend analysis 67 is directed at comparing the time expended on care. In this analysis, total surgical care time and total anesthesia care time is evaluated for all surgeons, anesthesiologists, procedures, ASA classification and protocols. Non-surgical anesthesia time data for each of these categories is also collected including P.A.C.U. time (post anesthesia care time), and post surgical hospital stay.

When the time/trend analysis indicates a positive, statistically significant relation of a particular surgeon or anesthetist with prolonged surgical, post-anesthesia care or hospital stay time, a review of the performance of the indicated individual is effected. Thereafter, based on such a review 64, recommendations are made in order to improve the efficiency of treatment. When the time/trend data analysis indicates a positive, statistically significant relation between a given protocol and excessive surgical and or anesthesia care time, the protocol is scrutinized. If it is determined that an agent or technique of the protocol is causing prolonged care time, then the protocol is modified 66 in order to eliminate the extended care time caused by the offending agent or technique.

A quality value trend analysis 69 indicates the relation of the two factors of cost and outcome data with:

a. anesthesiologist
b. protocol utilized
c. surgeon

In this trend analysis, a QV index value, is attributed to each anesthetic case based upon two factors; V, the cost of delivering care and Q, the quality of care. This analysis indicates the total quality of a provider's care since both the efficiency and quality of care are evaluated together. A positive, statistically significant correlation between a poor QV index and a given protocol will trigger a review 64 of the protocol for an offending agent and or technique and possible modification thereof. A positive relation between a provider and a poor QV will trigger a review, and possible modification 66 of that provider's care technique.

Figure 5:
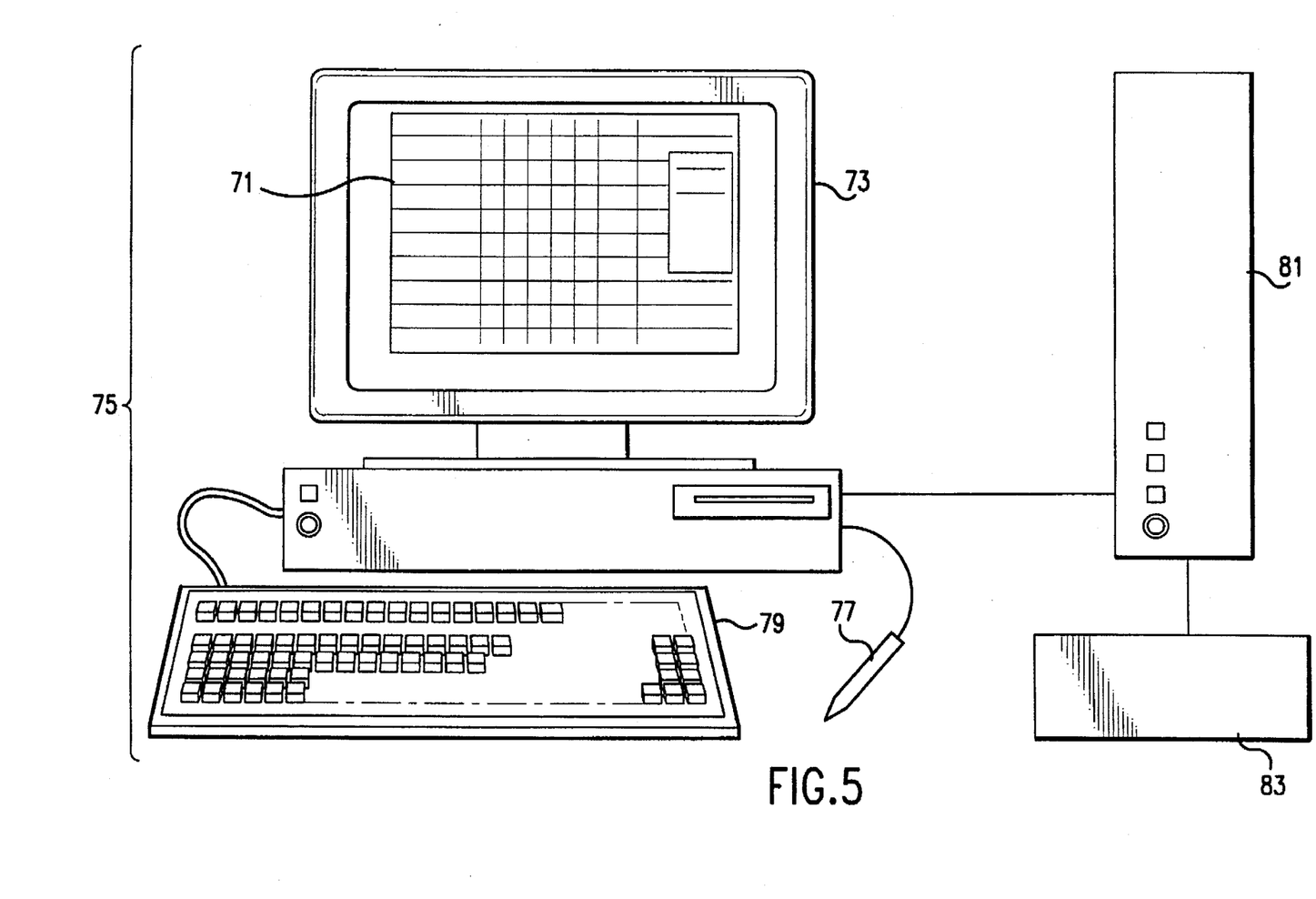
FIG. 5 is a flow chart illustrating an alternative preferred method of the present invention.

FIG. 5 illustrates an alternate preferred method of the present invention wherein the anesthetic and outcome records discussed above are provided as an image 71 on a computer CRT, LED or other monitor output 73 of a computer terminal 75. Data is entered within the records utilizing a pointing device such as a light pen 77 or mouse. Optionally a keyboard 79 may be utilized. The terminal is thereafter utilized to transmit the data to a central computer processor 81 and central data storage device 83. Thereafter, the data is subjected to the trend and cost analysis discussed above. In this embodiment, the anesthetic record displayed is, as in all preferred embodiments, similar to the format of conventional intra-operative anesthetic records.

The terms and expressions which have been employed in the foregoing specification are used therein as terms of description and not limitation, and there is no intention, in the use of such terms and expressions, of excluding equivalents of the features shown and described or portions thereof, it being recognized that the scope of the invention is defined and limited only by the following claims.

We claim:

1. A method of delivering operative anesthetic care during surgery comprising:

selecting an anesthetic protocol for a particular patient and procedure;

administering anesthetic care utilizing the selected protocol;

recording a
general systemic health type,
continuous medical status,
surgical procedure,
identity, dosage, amount and means of administration of all administered agents, and
outcome data for each anesthetic procedure and patient treated;

entering the recorded data into an integrated computerized data base;

subjecting said entered data to a computerized trend analysis;

identifying trend data indicating a statistically significant relation between protocols administered and suboptimal results of said anesthetic care; and modifying the selected protocol to eliminate or reduce said sub-optimal results and thus improve the delivered anesthetic care.

2. The method of claim 1 further comprising recording said data upon a scanable anesthetic record.

3. The method of claim 2 further comprising scanning said scanable record by means of a reading device and thereafter transmitting the data read by the device to a central data storage and processing means.

4. The method of claim 3 further comprising selecting the reading device to be of a telefacsimile type.

5. The method of claim 4 further comprising subjecting the transmitted data provided by the telefacsimile device to discrete field deciphering and verification utilizing an intelligent reader program resident within the computer processor and thereafter saving deciphered and verified data to the storage means.

6. The method of claim 1 further comprising entering the recorded data into a data base utilizing a computer terminal.

7. The method of claim 1 further comprising selecting a standardized set of practice protocols and restricting the protocols utilized to protocols of the standardized set.

8. The method of claim 1 further comprising recording the identity of the person administering said operative anesthetic care during surgery.

9. A method of delivering operative anesthetic care during surgery comprising:

selecting a standardized set of practice protocols;

administering anesthetic care utilizing only protocols selected from the standardized set;

recording a
general systemic health type,
continuous medical status,
surgical procedure,
the identity, dosage, amount and means of administration of all administered agents, and
outcome data for each anesthetic procedure and patient;

entering the recorded data into an integrated computerized data base;

subjecting the entered data to a computerized trend analysis;

identifying trend data indicating a statistically significant relation between protocols administered and suboptimal results of said anesthetic care; and modifying the selected protocol to eliminate or reduce sub-optimal anesthesia events.

10. The method of claim 9 further comprising recording said data upon a scanable anesthetic record.

11. The method of claim 10 further comprising scanning said scanable record by means of a reading device and thereafter transmitting the data read by the device to a central data storage and processing means.

12. The method of claim 11 further comprising selecting the reading device to be of a telefacsimile type.

13. The method of claim 12 further comprising subjecting the transmitted data provided by the telefacsimile device to discrete field deciphering and verification utilizing an intelligent reader program resident within computer processor and thereafter saving deciphered and read data to the storage means.

14. The method of claim 9 further comprising entering the recorded data into the data base utilizing a computer terminal.

15. The method of claim 9 further comprising recording the identity of the person delivering said operative anesthetic care during surgery.

16. A method of delivering operative anesthetic care during surgery comprising:

selecting an anesthetic protocol for a particular patient and procedure;

administering anesthetic care utilizing the selected protocol;

recording the
general systemic health status,
continuous medical status,
surgical procedure,
the identity, dosage, amount and means of administration of all administered agents, and
outcome data for each anesthetic procedure and patient entering the recorded data into an integrated computerized data base;

entering agent and materials cost data into the data base;

subjecting said entered data to a computerized outcome trend analysis;

subjecting said data base to a computerized cost trend analysis;

identifying outcome trend data indicating a statistically significant relation between agent/protocol administered and suboptimal results of said anesthetic care;

identifying cost trend analysis indicating a statistically significant relation between protocols/agent and increased cost of delivered care; and modifying the selected protocols in accordance with the outcome trend analysis and cost trend analysis in order to eliminate or reduce suboptimal outcomes and reduce the cost of delivered anesthetic care.

17. The method of claim 16 further comprising recording the entered data upon a scanable anesthetic record.

18. The method of claim 17 further comprising scanning the scanable record by means of a reading device and thereafter transmitting the data read by the reading device to a central data storage and processing means.

19. The method of claim 18 further comprising selecting the reading device to be of a telefacsimile type.

20. The method of claim 19 further comprising subjecting the transmitted data provided by the telefacsimile device to discrete field deciphering and verification utilizing an intelligent reader program incorporated within a computer processor and saving deciphered and verified data to the storage means.

21. The method of claim 16 further comprising entering the recorded data into a data base utilizing a computer terminal.

22. The method of claim 16 further comprising selecting a standardized set of practice protocols and restricting the protocols administered to the standardized set.

23. The method of claim 16 further comprising recording the identity of the person delivering said operative anesthetic care during surgery.

24. A method of delivering operative anesthetic care during surgery comprising:

selecting a standardized set of practice protocols;

restricting delivered anesthetic care to protocols selected from the standardized set;

administering anesthetic care utilizing the selected protocol;

recording a
general systemic health type,
continuous medical status,
surgical procedure,
the identity, dosage, amount and means of administration of all administered agents; and
outcome data for each anesthetic procedure and patient;

entering the recorded data into an integrated computerized data base;

entering agent and materials cost data into the data base;

subjecting the entered data to a computerized outcome trend analysis;

subjecting the data base to a computerized cost trend analysis;

identifying outcome trend data indicating a statistically significant relation between protocols or providers and suboptimal results of said anesthetic care;

identifying cost trend analysis indicating a statistically significant relation between protocols or providers and increased cost of delivered care; and modifying the selected protocols to eliminate or reduce sub-optimal outcomes and cost.

25. The method of claim 24 further comprising recording said data upon a scanable anesthetic record.

26. The method of claim 25 further comprising scanning the data entered upon the scanable record by means of a reading device and thereafter transmitting the data read by the device to a central data storage and processing means.

27. The method of claim 26 further comprising selecting the reading device to be of a telefacsimile type.

28. The method of claim 27 further comprising subjecting data transmitted by the telefacsimile device to discrete field deciphering and verification utilizing an intelligent reader program incorporated within a computer processor and thereafter saving the deciphered and verified data to the storage means.

29. The method of claim 24 further comprising entering the recorded data into a data base utilizing a computer terminal.

30. The method of claim 24 further comprising recording anesthetic service provider identification data for each anesthesia case.

* * * * *